United States Patent [19]

Campbell et al.

[11] 4,391,402

[45] Jul. 5, 1983

[54] SURGICAL STAPLING CONTROL MEANS

[75] Inventors: Jay E. Campbell, Upper Black Eddy; Richard H. Reichmann, Churchville, both of Pa.; Lehmann K. Li, Fairfield, Conn.

[73] Assignee: American Cyanamid Company, Stamford, Conn.

[21] Appl. No.: 191,653

[22] Filed: Sep. 26, 1980

Related U.S. Application Data

[63] Continuation-in-part of Ser. No. 153,229, May 27, 1980, abandoned.

[51] Int. Cl.³ .............................................. A61B 17/04
[52] U.S. Cl. ..................................... 227/121; 227/19; 227/DIG. 1; 128/334 R
[58] Field of Search ..................... 227/19, DIG. 1, 83, 227/107, 114, 115, 116, 117, 120, 121, 139, 149, 156; 128/334 R; 72/410

[56] References Cited

U.S. PATENT DOCUMENTS

| | | | |
|---|---|---|---|
| 1,271,548 | 7/1918 | Doig | 227/121 |
| 2,707,783 | 5/1955 | Sullivan | 72/410 |
| 3,873,016 | 3/1975 | Fishbein | 227/83 |
| 3,905,535 | 9/1975 | Novak et al. | 227/120 |
| 4,108,306 | 8/1978 | Samuels et al. | 227/121 X |
| 4,109,844 | 8/1978 | Becht | 227/120 |
| 4,179,057 | 12/1979 | Becht et al. | 227/120 X |
| 4,196,836 | 4/1980 | Becht | 227/19 |
| 4,202,480 | 5/1980 | Annett | 227/121 X |
| 4,204,623 | 5/1980 | Green | 227/121 X |

Primary Examiner—Paul A. Bell
Attorney, Agent, or Firm—Charles F. Costello, Jr.

[57] ABSTRACT

A surgical stapling control means has been invented. The control means are contained in a surgical instrument comprising a handle; a trigger pivotally attached and on compression internal to said handle; and staple forming means contained in the forward portion of the handle.

The control means comprise a mult-toothed ratchet on the rearward portion of the trigger; at least one guide pin attached to the initial end of the ratchet; a nonpivoting pawl attached to the rearward portion of the handle to coordinate with the ratchet; guide means adjacent the rearward portion of the handle to coordinate with and provide tension to the guide pins.

On partially compressing the trigger, the guide means provide tension on the guide pins and the ratchet engages the pawl. On completely compressing the trigger, the guide pins cross over the top of the guide means causing the ratchet to be disengaged from the pawl.

6 Claims, 29 Drawing Figures

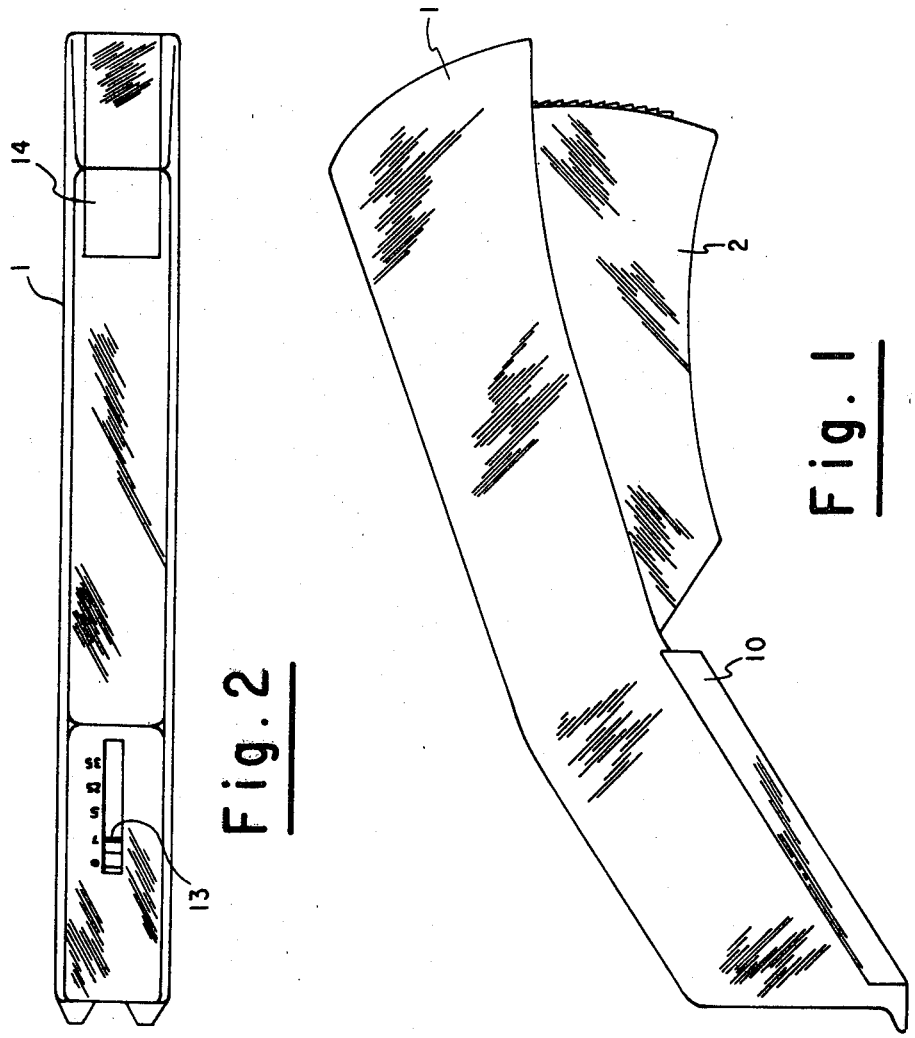
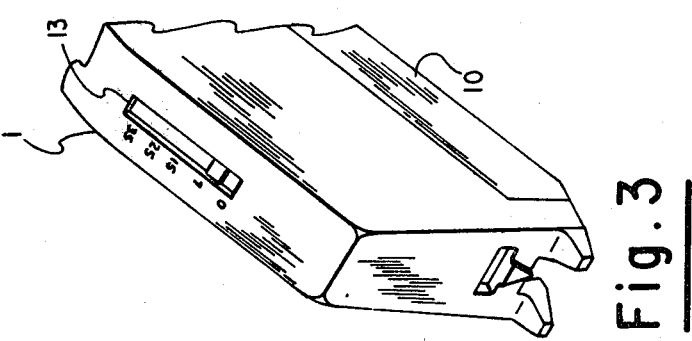

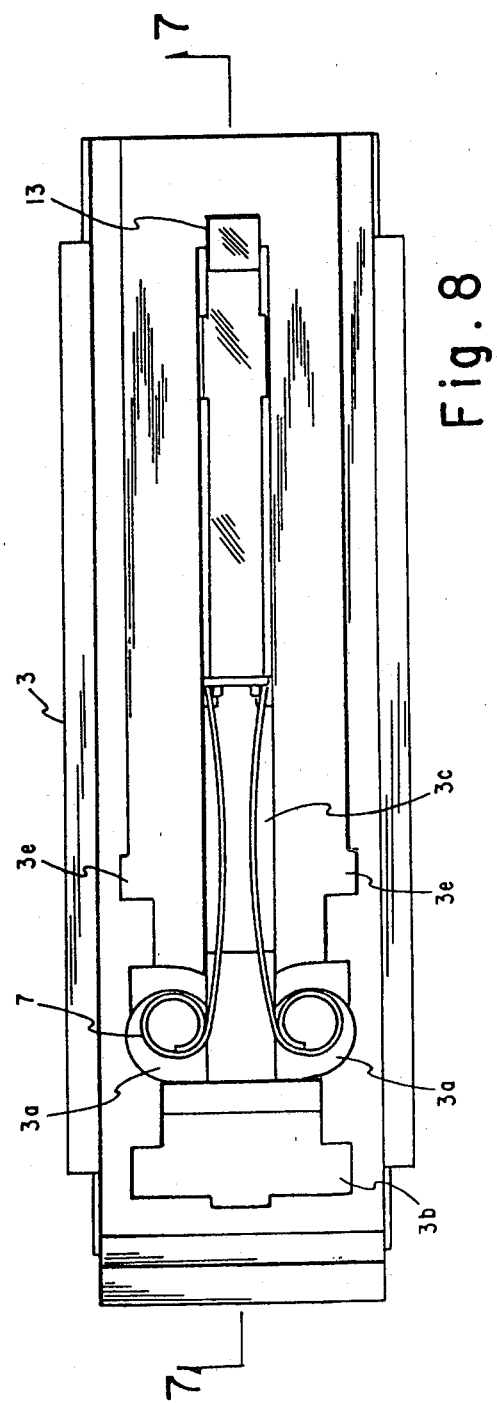
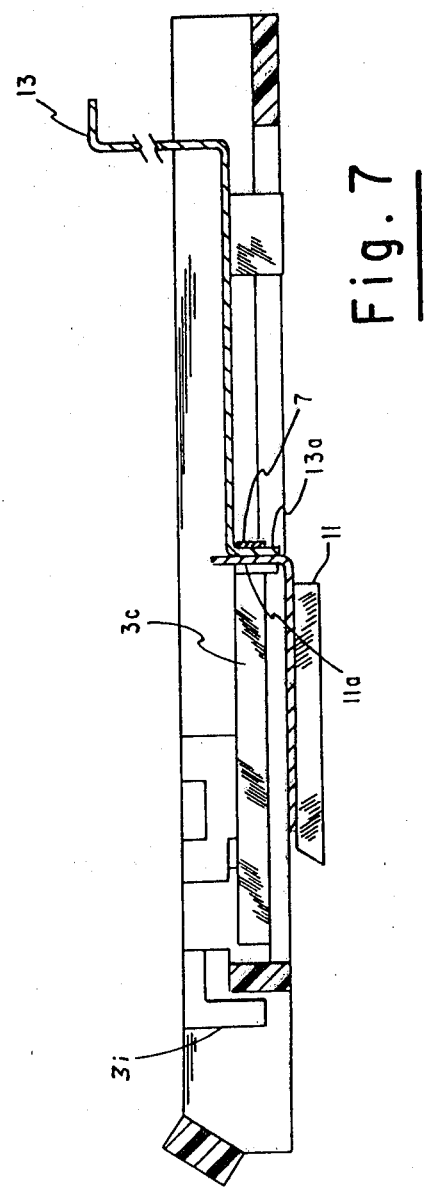

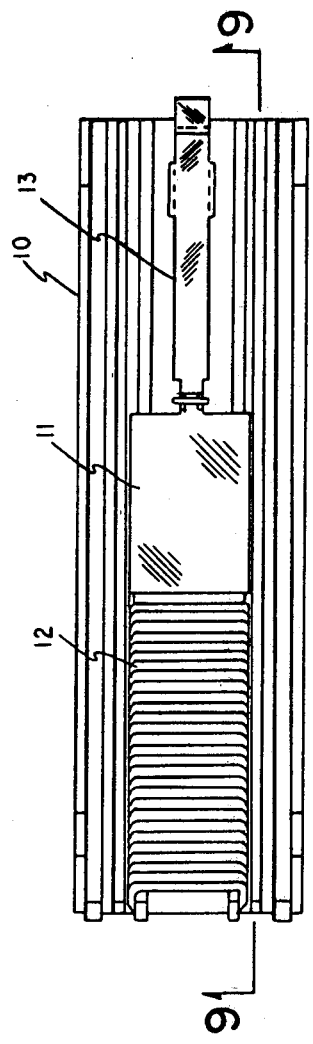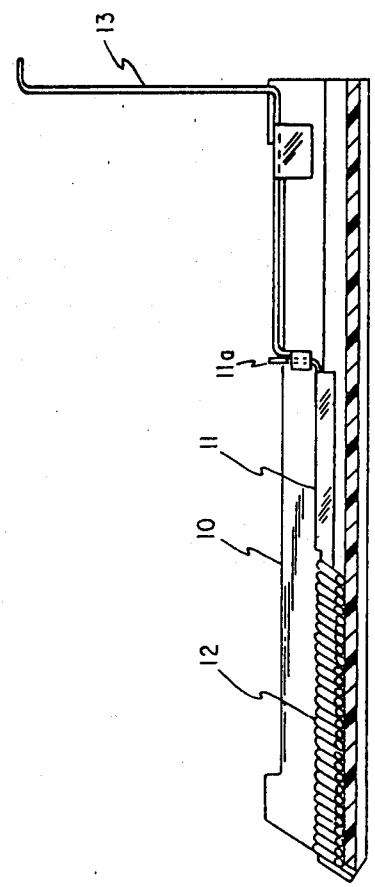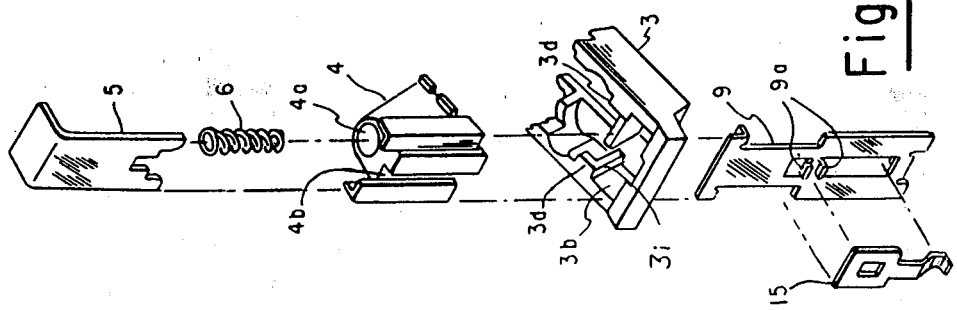

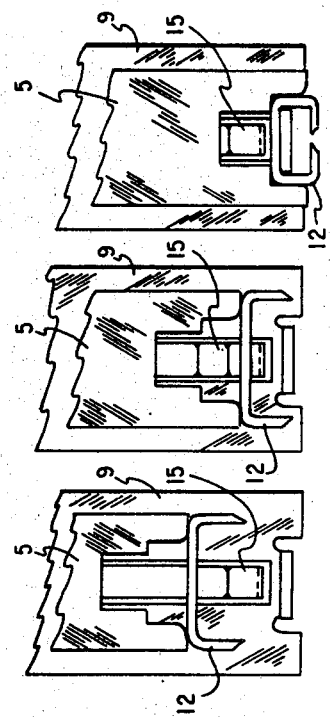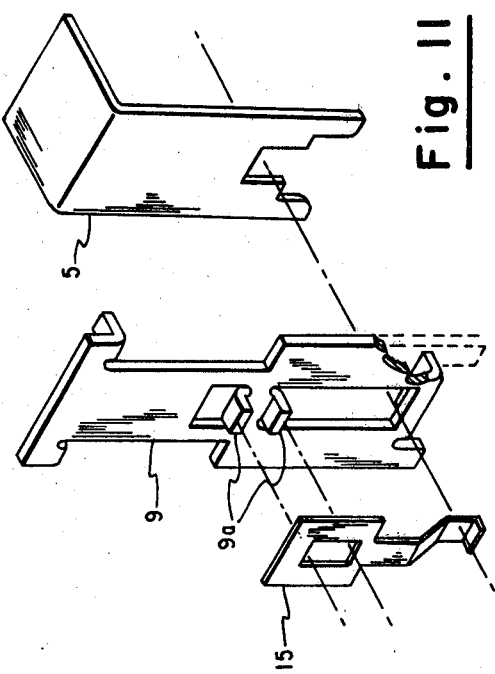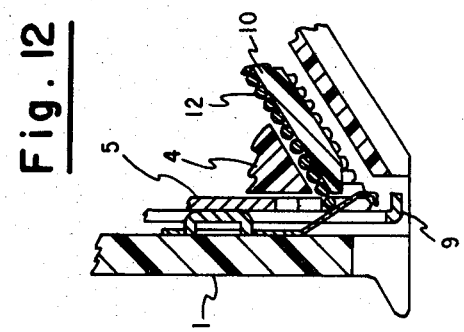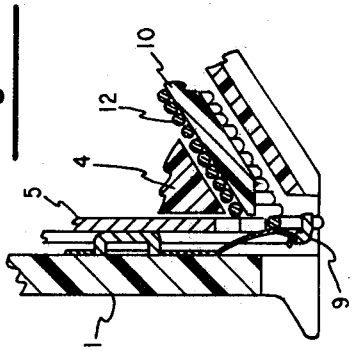

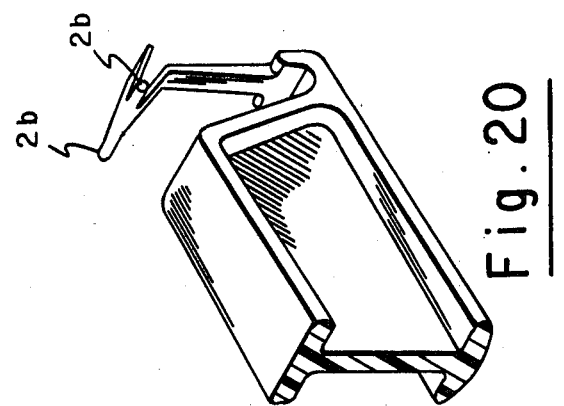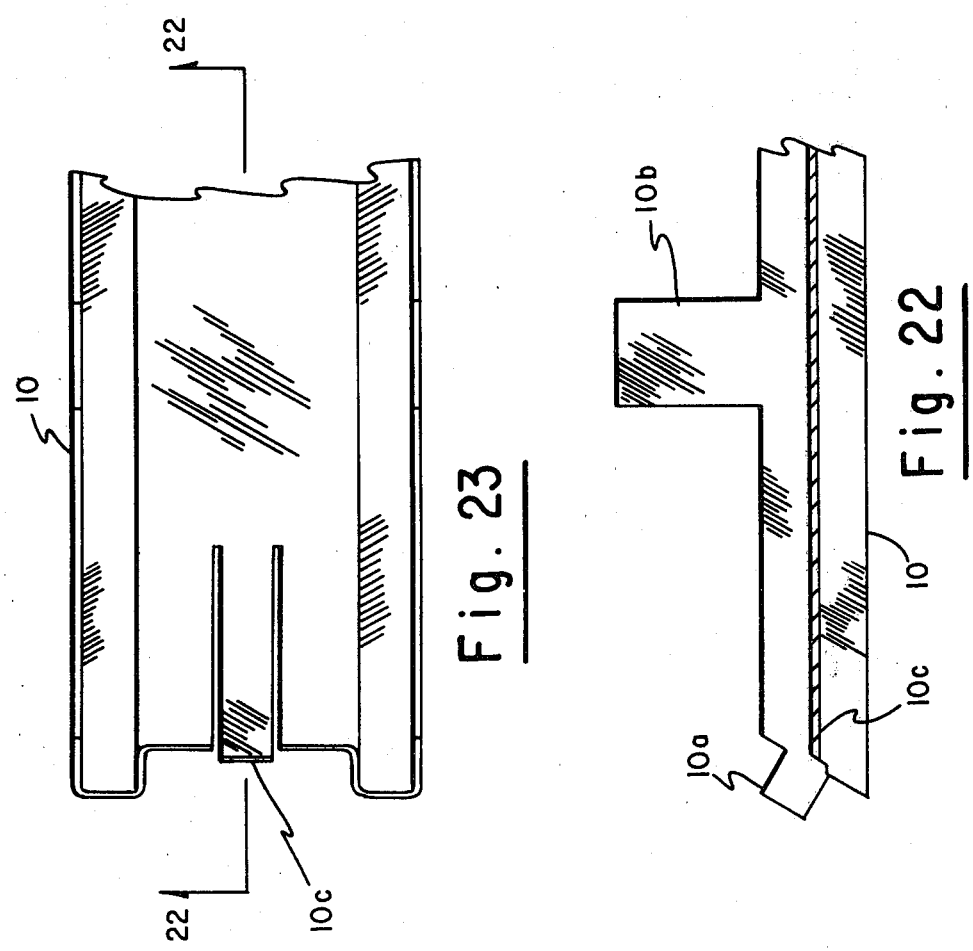

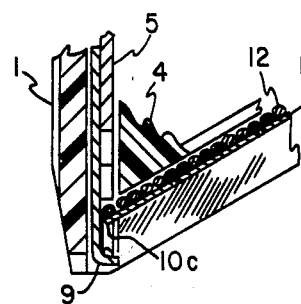 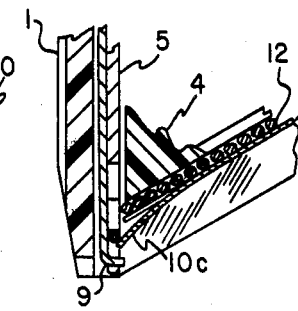 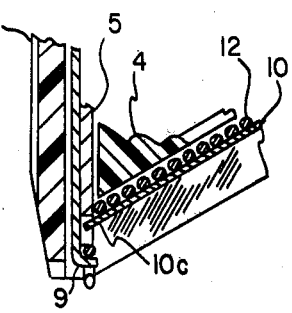
Fig. 25　Fig. 26　Fig. 27
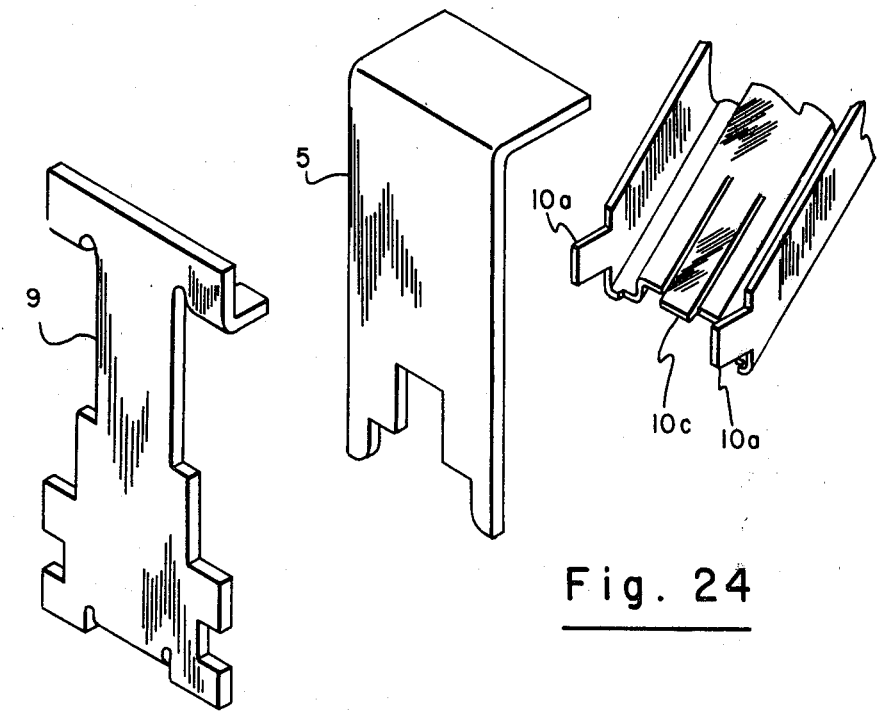
Fig. 24

SURGICAL STAPLING CONTROL MEANS

CROSS REFERENCE TO RELATED APPLICATIONS

This is a continuation-in-part application of U.S. application Ser. No. 153,229 filed May 27, 1980, now abandoned.

BACKGROUND AND SUMMARY OF THE INVENTION

This invention relates to a surgical stapling control means which prevents the trigger in a stapling instrument from partially forming a staple and then returning and picking up the next staple.

The Applicants are not aware of any prior art references which in their judgements as persons skilled in the art would anticipate or render obvious the control means of this invention. However, to develop the background of the invention and to establish the state of the art, the following reference is cited. U.S. Pat. No. 3,873,016, which is incorporated by reference. This reference discloses a stapling instrument including a ratchet means.

The surgical stapling control means has advantages over the prior art reference. The control means prevents the trigger from returning to its initial position if the compression is interrupted. Thus has the advantage of preventing a second staple from being formed on the anvil flange before a first staple is separated from the instrument. Another advantage of the control means is interrupted stapling. The surgeon can now stop the compession of the trigger into the handle to realign the instrument over the wound site. Thus the possibility of a perfect stapling procedure is greatly enhanced. Finally, the control means are automatically disengaged on completely compressing the trigger. Thus, the control means do not have to be manually reset after a single staple is formed and separated from the instrument.

A surgical stapling control means has now been invented. The control means are contained in a surgical instrument comprising a handle; a trigger pivotally attached and on compression internal to said handle; and staple forming means contained in the forward portion of the handle.

The control means comprise a multi-toothed ratchet on the rearward position of the trigger; at least one guide pin attached to the initial end of the ratchet; a nonpivoting pawl attached to the rearward portion of the handle to coordinate with the ratchet; and guide means adjacent the rearward portion of the handle to coordinate with and provide tension to the guide pin.

An alternative surgical stapling control means has also been invented. The control means are contained in a surgical instrument comprising a handle; a trigger pivotally attached and on compression internal to said handle; and staple forming means contained in the forward portion of said handle.

The alternative control means comprise a multi-toothed ratchet on the rearward portion of the handle; a pawl attached to the rearward portion of the trigger to coordinate with the ratchet; at least one guide pin attached to the initial end of the pawl; and guide means adjacent the rearward portion of said handle to coordinate with and provide tension to the guide pin.

On partially compressing the trigger the guide means provide tension on the guide pin and the ratchet engages the pawl. On completely compressing the trigger, the guide pin crosses over the top of the guide means causing the ratchet to be disengaged from the pawl.

In one embodiment the guide means described above are two cams attached to each side of the handle. In another embodiment, the stapling control means comprises two guide pins to coordinate with the two cams.

In yet another embodiment, the staple forming means described above is a track; a plurality of staples loaded and staple advancing means carried on the track; a track cover mounted on the track; an anvil surface mounted and a first bias means movably mounted on the cover, the said anvil surface terminating in a perpendicular flange; a staple adjacent the anvil surface; a retainer spring mounted on the anvil surface or a leaf spring on the terminal end of the track, and separating the staple from the flange; a guide block mounted on the cover adjacent the anvil surface; and a forming blade and a second bias means movably mounted on the guide means, the forming blade and the trigger having coordinating surfaces. The trigger has "overtravel". That is on compressing the trigger into the handle the staple forms on the flange before the guide pins cross over the top of the guide means causing the ratchet to be disengaged from the pawl.

In still another embodiment of the staple forming means described above, the track cover is adjacent the forward portion of the trigger. In still yet another embodiment of the staple forming means, the forming blade is between the forward portion of the cover and the anvil surface.

In yet another embodiment the stapling instrument described above comprises an indicator to indicate the number of staples remaining in the instrument. The indicator has an initial end visible in the handle. A terminal end is movably mounted on the staple advancing means such that on releasing the trigger, the first bias means pulls the terminal end and thus moves the initial end of the indicator.

A method of using the stapling instrument is within the scope of this invention.

A method of closing a wound or of connecting skin or fascia comprises: joining the adjacent edges of the wound or skin or fascia; placing the stapling instrument described above adjacent to the would or to the skin or fascia; compressing the trigger into the handle; and releasing the trigger and advancing the instrument, whereby a formed staple is placed between the edges.

DESCRIPTION OF THE DRAWINGS

FIGS. 1 and 2 are side and top views respectively of the stapling instrument;

FIG. 3 is a broken perspective view of the front portion of the instrument shown in FIGS. 1 and 2;

FIGS. 7 and 8 are sectional side, and top views respectively of the instrument track cover;

FIGS. 9 and 10 are sectional side, and top views respectively of the instrument track;

FIG. 11 is an expanded view showing the relationship of the forming blade, bending anvil and retainer spring; and FIGS. 12 and 13 are broken and sectional side views of FIG. 1 showing the position and relationship of the staple and retainer spring in the initial position and on compressing the instrument trigger;

FIGS. 14 to 16 are broken rear views of the bending anvil showing the relationship of the staple, forming blade, retainer spring and anvil flange during compression of the instrument trigger;

FIG. 17 is an expanded view showing the relationship of the forming blade, first bias means, guide block, track cover, bending anvil and retainer spring.

FIG. 20 is a broken perspective view of the alternative control means in the trigger;

FIGS. 22 and 23 are broken sectional side and top views, respectively of the instrument track shown in FIG. 21;

FIG. 24 is an expanded view showing the relationship of the forming blade, bending anvil and leaf spring shown in FIG. 21; and FIGS. 25 to 27 are broken and sectional side views showing respectively the position and relationship of the staple and leaf spring in the initial position, on partial compressing and on complete compressing of the instrument trigger.

DESCRIPTION OF THE PREFERRED EMBODIMENT

Figures 4A, 4B:
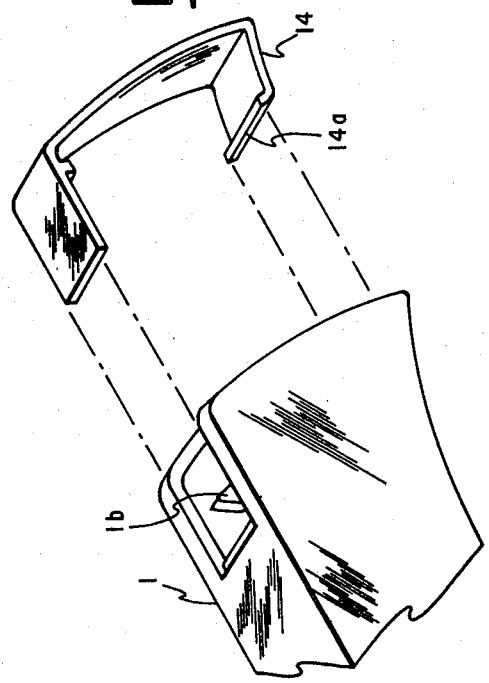
FIGS. 4A and 4B are perspective views showing the parts of the stapling instrument control means in the handle and in the handle cover, respectively.

Referring to FIGS. 1 to 3, the instrument comprises a handle 1 and a trigger 2. A staple track 10 (more fully described in FIGS. 6 and 9 to 10) is inserted and attached to the forward portion of the handle 1, for example by cementing or sonic welding. The initial end of an indicator 13 is visible through an opening in the forward top portion of the handle 1. A combined ratchet stop and cover 14 (more fully described in FIGS. 4 and 5) is attached to the rear portion of handle 1.

Referring to FIGS. 6 to 11 and 17, the track cover 3 is assembled as follows. The first bias means 7, which preferably is a negatory spring, is mounted into the openings 3a in track cover 3. Retainer spring 15 is inserted onto bending anvil retainer tabs 9a. The bending anvil 9 and the retainer spring 15 are then placed through the opening 3b. The terminal end 13a of indicator 13 is mounted onto the track cover 3 in front of the spring 7 and protrudes through the bottom 3c of the track cover 3.

The guide block 4 is mounted under tabs 3d. A locking wedge 8 is then pushed into slots 3e to hold the guide block 4 on the track cover 3. Other means for holding the guide block on the track cover can be used, for example bonding, riveting, peening, tacking or welding.

The second bias means 6, preferably a spring, is inserted into the guide block opening 4a. The forming blade 5 is mounted through the guides 4b in the guide block. The vertical surface of the forming blade 5 is between the forward portion 3i of the track cover 3 and the anvil surface 9.

Referring specifically to FIGS. 9 and 10, staples 12 are loaded onto the track 10. The staple advancing means, preferably a staple pusher 11 is carried on the track 10 behind the staples 12 by the first bias means 7 (shown e.g., in FIG. 8). The indicator 13 is carried with the staple pusher 11 by the first bias means 7. The staples 12 in FIGS. 9 and 10 are shown in their orientation when the instrument is in the position shown in FIG. 1.

The track cover 3 is then mounted onto the track 10 for example by sonic welding. The spring 7 is then attached to the advancing means tab 11a by pulling back on the indicator 13 and engaging the center of the extended spring 7 with the advancing means tab 11a. The trigger pivots 2aa are placed against stops in the forward portion of the handle 1. The track cover 3 and track 10 are then inserted and attached to the forward portion of the handle 1, for example by cementing or sonic welding. The trigger pivots 2aa are thus captured.

Referring to FIGS. 12 to 17, the stapling instrument is used by placing the anvil surface 9 adjacent a wound opening or between skin or fascia. The trigger 2 is then compressed into the handle 1 (shown in FIG. 1). The front end of trigger 2 engages the top flange of forming blade 5, forcing it down thru the guides 4b on guide block 4. The lower edges of the forming blade have a recessed area to engage staple 12. The staple is pushed downward and forced to bend at right angles on either side of the lower flange of anvil 9.

In the initial or rest position, the staple 12 is adjacent the vertical surface of the anvil 9, as shown in FIG. 12. The forming blade 5 lowers and pushes the staple downward and onto the anvil flange. The forming of the staple around the anvil lower flange is well known in prior art, e.g., as described in U.S. Pat. No. 4,014,492 issued Mar. 29, 1977 which is incorporated herein by reference. By releasing the trigger and advancing the instrument, the staple 12 is separated from the anvil flange.

When releasing trigger 2, spring 6 returns forming blade 5 and trigger 2 to their relaxed positions. Spring 7 pulls against pusher 11 to advance the plurality of staples. Each time trigger 2 is compressed indicator 13 advances with pusher 11. An indication of the staple depletion appears in the opening in the top forward portion of handle 1.

Figure 5:
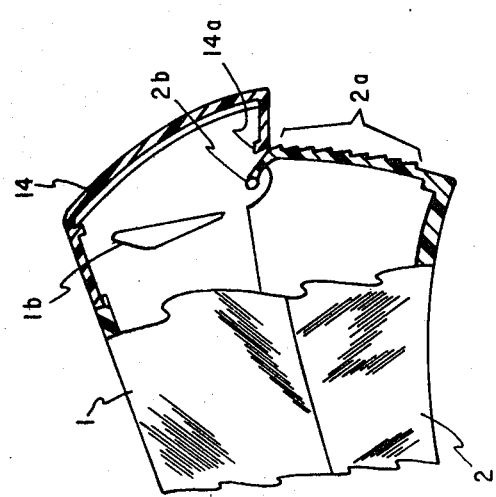
FIG. 5 is a broken sectional view of the stapling instrument control means.

Referring to FIGS. 4 and 5, to prevent partially compressing the trigger 2, partially forming a staple 12, and then allowing the trigger to return and pick up the next staple, a multi-toothed ratchet 2a is built into the rear of the trigger 2 and cam guides 1b into handle 1. When the trigger 2 is compressed, the ratchet 2a engages stop 14a and prevents the trigger from returning to its relaxed position. The trigger must be compressed past the last ratchet tooth 2a and must be completely closed so that the guide pins 2b (more fully shown in FIG. 6) move up and cross over the cam guides 1b.

The guide pins are spring loaded. Thus when the trigger is completely compressed, the guide pins cross over the top of the cam guides 1b. On releasing the trigger from a final compression, the ratchet is thus prevented from locking on the stop 14a.

Figure 18A:
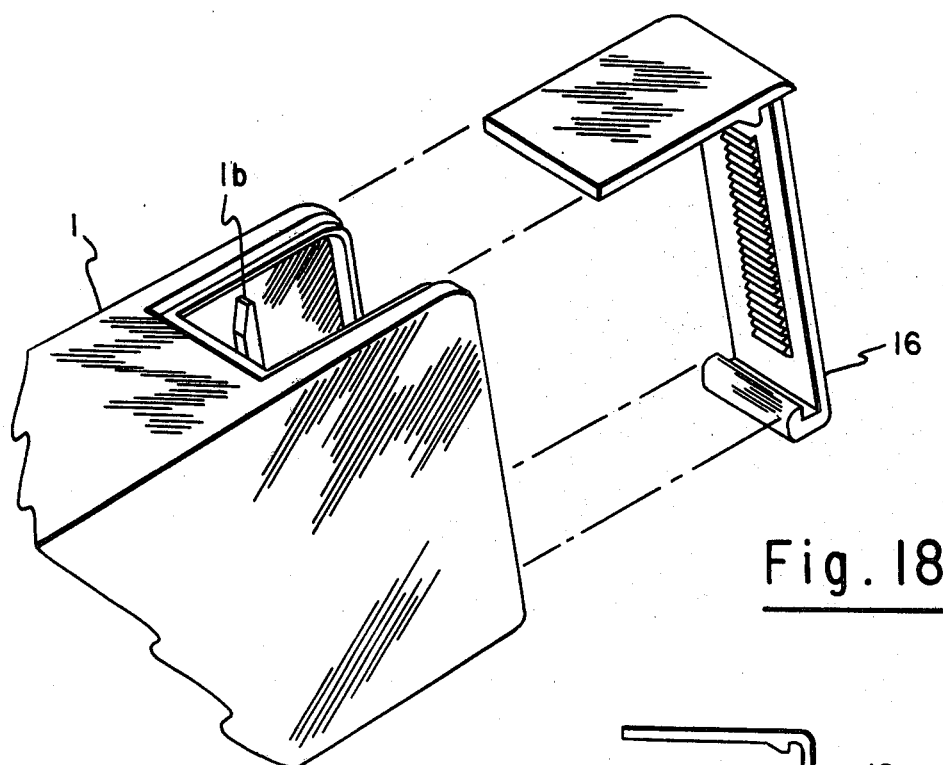
FIGS. 18A and 18B are perspective views showing an alternative embodiment of the stapling instrument control means.
Figure 18B:
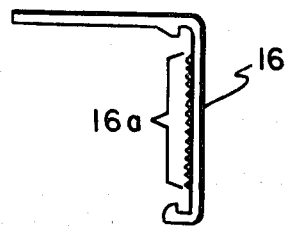
Figure 19:
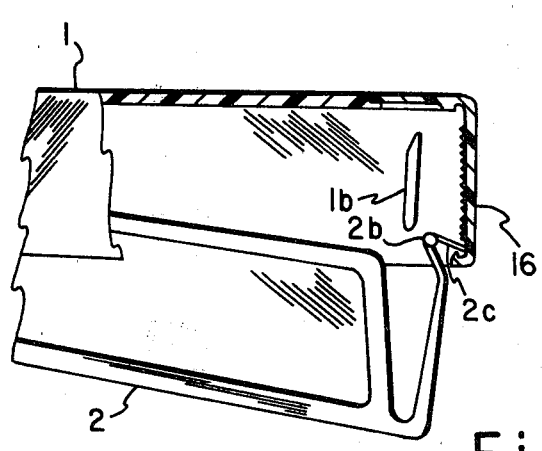
FIG. 19 is a broken sectional view of the alternative stapling instrument control means of FIG. 18.

Referring to FIGS. 18 and 19 showing an alternative embodiment of the stapling instrument control means, to prevent partially compressing the trigger 2, partially forming a staple 12, and then allowing the trigger to return and pick up the next staple, a multi-toothed ratchet 16a is built into the cover 16. A stop 2c is built into the trigger 2. Cam guides 1b are built into handle 1.

When the trigger 2 is compressed, the ratchet 16a engages stop 2c and prevents the trigger from returning to its relaxed position. The trigger must be compressed past the last ratchet tooth 16a and must be completely closed so that the guide pins 2b (more fully shown in FIG. 6) move up and cross over the cam guides 1b.

The guide pins 2b are spring loaded. Thus when the trigger is completely compressed, the guide pins cross over the top of the cam guides 1b. On releasing the trigger from a final compression, the ratchet is thus prevented from locking on the stop 2c.

Figure 21:
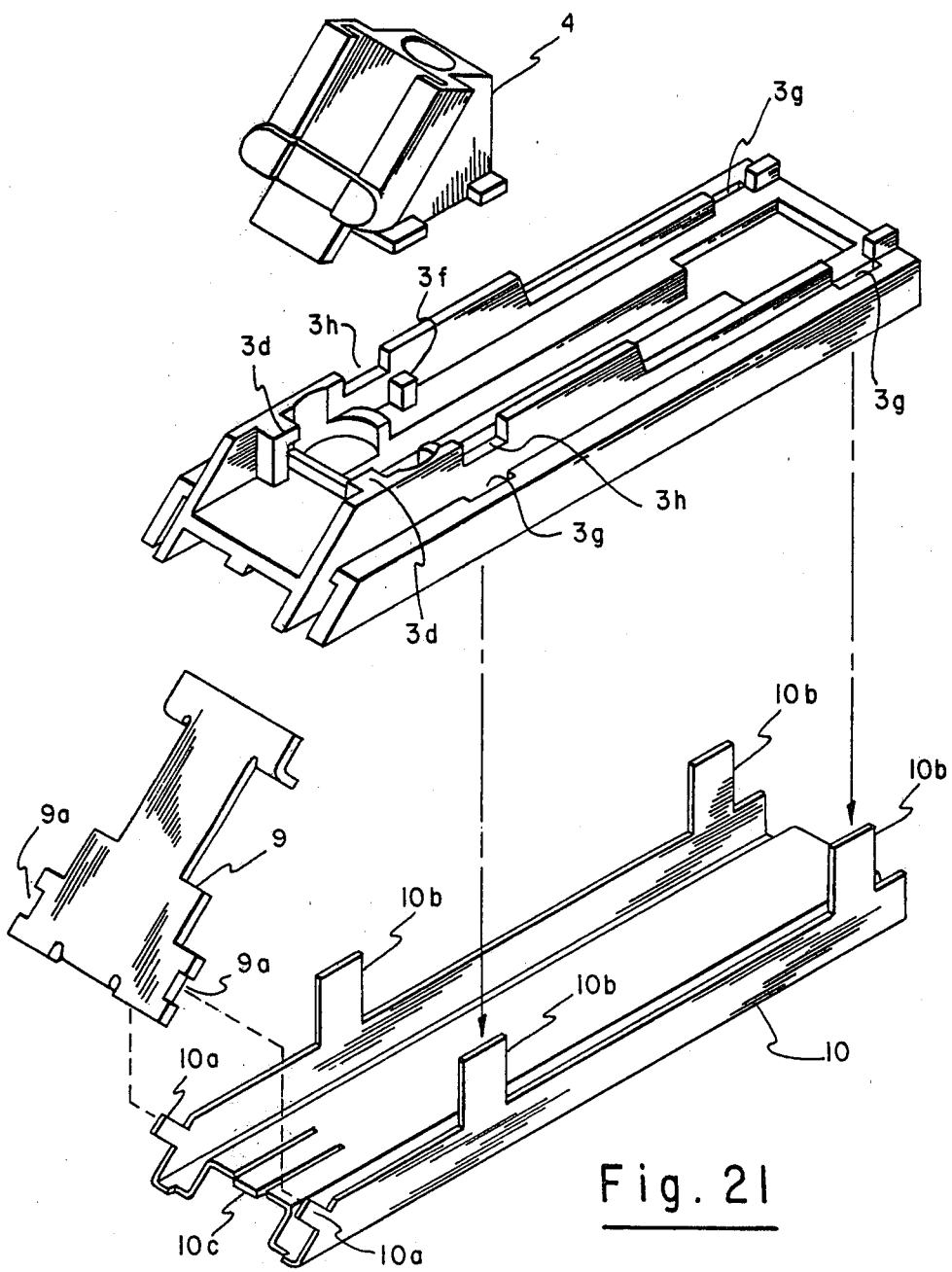
FIG. 21 is an expanded view of an alternative embodiment of the track and track cover.

Referring to FIGS. 20 and 21 which show respectively, the alternative control means in the trigger and an alternative embodiment of the track and track cover, the track cover 3 is assembled as follows. The forward portion 3i of the track cover can be identical to that shown in FIGS. 6 to 8. The bias means 7 (not shown) and the bending anvil 9 can be mounted identically to the description in FIGS. 6 to 8 and 17. The front tabs 10a on the track 10 pass through the slots 9a and then fold onto the bending anvil 9. As shown more fully in FIG. 24, the front tabs 10a and the slots 9a are sufficiently wide to allow the forming blade 5 to move. The terminal end 13a of indicator 13 (not shown) is mounted identically to the description in FIGS. 6 to 10.

The guide block 4 is mounted under tabs 3d as shown in FIGS. 6 to 8 and 17. Blocks 3f are adjacent slots 3h on the track cover 3. Blocks 3f diagonally support the guide block 4 on the track cover 3. Forward vertical tabs 10b on the track 10 pass through the forward openings 3g in the track cover 3 and then fold onto the portion of the guide block 4 in slots 3h to hold the guide block on the track cover. Rear vertical tabs 10b pass through the rear openings 3g and then fold onto the track cover 3.

Figure 6:
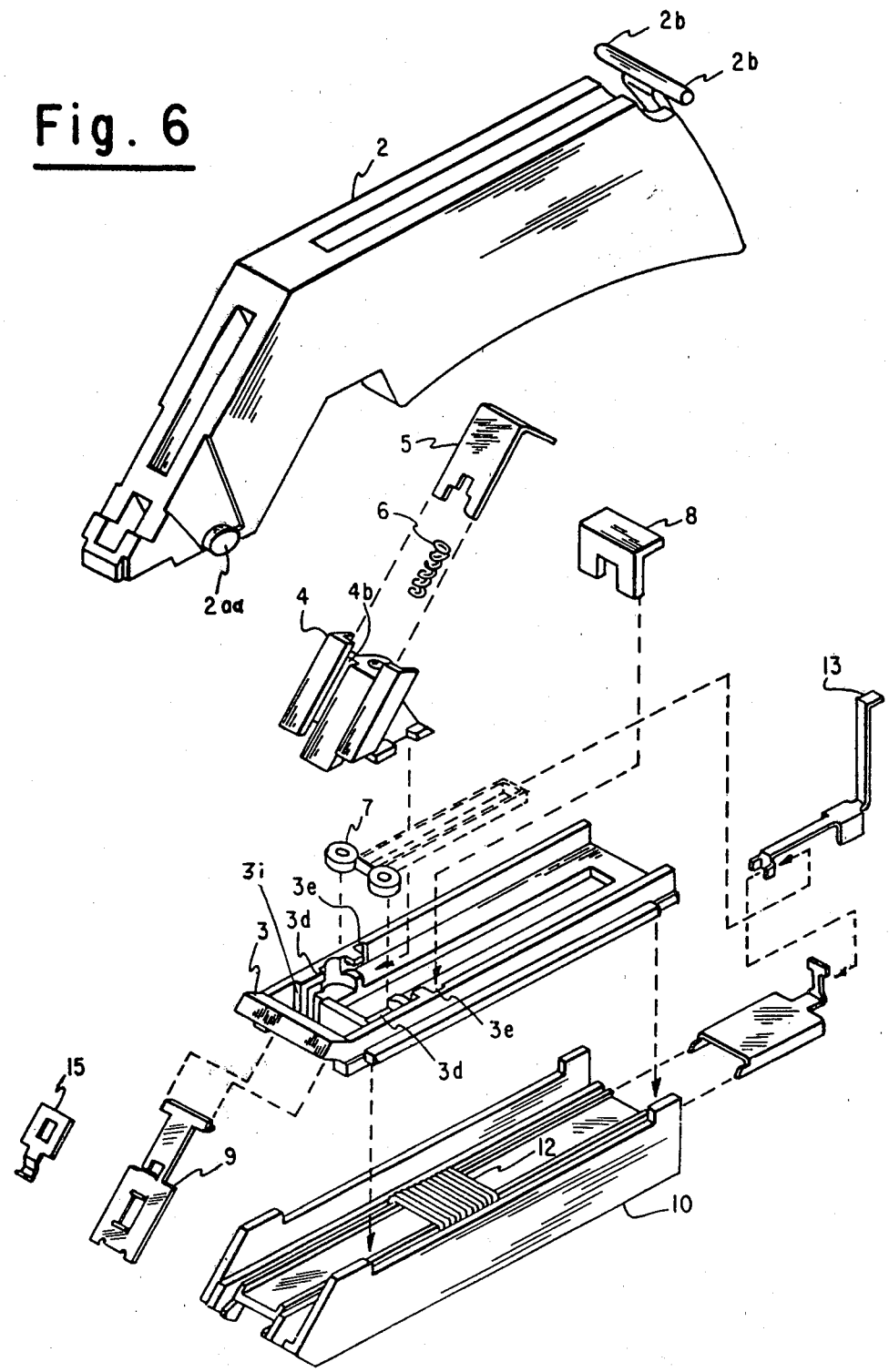
FIG. 6 is a perspective view of the instrument trigger, and an expanded view of the track and track cover.

The second bias means 6 and the forming blade 5 are mounted identically to the description in FIGS. 6 and 17.

FIGS. 22 and 23 show an alternative embodiment of the track 10. In the alternative embodiment, the track 10 contains a leaf spring 10c on the terminal end of the track. The leaf spring separates the staple adjacent to the anvil surface from the anvil flange. The staples 12, staple advancing means 11, and indicator 13 are carried on the track 10 and are identical to the description in FIGS. 9 and 10. Referring to FIGS. 22 to 27, the stapling instrument with the alternative embodiment is used by placing the anvil surface 9 adjacent a wound opening or between skin or fascia. The trigger 2 (shown in FIG. 1) is then compressed into the handle 1. The front end of trigger 2 engages the top flange of forming blade 5, forcing it down thru the guides 4b (shown in FIG. 17) on guide block 4. The lower edges of the forming blade have a recessed area to engage staple 12. The staple is pushed downward and displaces the leaf spring 10c. The leaf spring 10c then moves back to its initial position to hold the next staple at the terminal end of track 10 and adjacent the anvil surface. The forming blade 5 continues to engage staple 12 which is then forced to bend at right angles on either side of the lower flange of anvil 9.

In the initial or rest position, the staple 12 is adjacent the vertical surface of the anvil 9, as shown in FIG. 25. The forming blade 5 lowers and pushes the staple downward and onto the anvil flange. By releasing the trigger and advancing the instrument, the staple 12 is separated from the anvil flange.

We claim:

1. A surgical stapling control means comprising a handle; a trigger pivotally attached and compressible into said handle; a staple forming means contained in the forward portion of said handle; a flexible arm mounted on the rearward portion of said trigger; a pawl and at least one guide pin attached to one end of said arm; a multi-toothed ratchet attached to the rearward portion of said handle; and guide means having upper and lower portions, said guide means positioned adjacent the rearward portion of said handle so as to coordinate with and provide tension to said guide pin, such that on partially compressing said trigger the lower portion of said guide means provides tension on said guide pin and flexes said arm such that the pawl engages said ratchet and such that on complete compression of said trigger, the upper portion of said guide means releases tension from said guide pin allowing said arm to relax and allowing said guide pin to cross over said guide means, thus causing said pawl to be disengaged from said ratchet.

2. The surgical stapling control means of claim 1 wherein the lower portion of said guide means comprises two cams attached to each side of said handle.

3. The surgical stapling control means of claim 2 wherein two guide pins are attached to one end of said arm and coordinate with said cams.

4. A surgical stapling control means comprising a handle; a trigger pivotally attached and compressible into said handle; a staple forming means contained in the forward portion of said handle; a multi-toothed, flexible ratchet arm formed on the rearward portion of said trigger; at least one guide pin attached to one end of said ratchet arm; a nonpivoting pawl attached to the rearward portion of said handle to coordinate with said ratchet arm; and guide means having upper and lower portions, said guide means positioned adjacent the rearward portion of said handle so as to coordinate with and provide tension to said guide pin, such that on partially compressing said trigger the lower portion of said guide means provides tension on said guide pin and flexes said ratchet arm into engagement with said pawl and on complete compression of said trigger, the upper portion of said guide means releases tension from said guide pin allowing said ratchet arm to relax and allowing said guide pin to cross over said guide means, thus causing said ratchet to be disengaged from said pawl.

5. The surgical stapling control means of claim 4 wherein the lower portion of said guide means comprises two cams attached to each side of said handle.

6. The surgical stapling control means of claim 5 wherein two guide pins are attached to one end of said ratchet arm and coordinate with said cams.

* * * * *